(12) United States Patent
Morin et al.

(10) Patent No.: US 7,029,438 B2
(45) Date of Patent: Apr. 18, 2006

(54) ANOSCOPE

(75) Inventors: Marc G. Morin, North Vacouver (CA); Patrick J. O'Regan, Riyadh (SA)

(73) Assignee: Medsurge Medical Products, Corp., Vancouver (CA)

( * ) Notice: Subject to any disclaimer, the term of this patent is extended or adjusted under 35 U.S.C. 154(b) by 252 days.

(21) Appl. No.: 10/301,492

(22) Filed: Nov. 20, 2002

(65) Prior Publication Data

US 2003/0130559 A1    Jul. 10, 2003

(51) Int. Cl.
*A61B 17/32* (2006.01)
(52) U.S. Cl. .................................. 600/184; 600/114
(58) Field of Classification Search .............. 600/200, 600/114, 184–246
See application file for complete search history.

(56) References Cited

U.S. PATENT DOCUMENTS

| 4,215,678 | A | * | 8/1980 | Heine et al. | 600/182 |
|---|---|---|---|---|---|
| 4,306,546 | A | * | 12/1981 | Heine et al. | 600/160 |
| 4,527,553 | A | * | 7/1985 | Upsher | 600/188 |
| 4,538,594 | A | * | 9/1985 | Boebel et al. | 600/102 |
| 4,690,132 | A | * | 9/1987 | Bayer et al. | 600/219 |
| 4,819,620 | A | * | 4/1989 | Okutsu | 600/114 |
| 4,834,067 | A | * | 5/1989 | Block | 600/184 |
| 5,165,387 | A | * | 11/1992 | Woodson | 600/184 |
| 5,249,568 | A | * | 10/1993 | Brefka et al. | 600/184 |
| 5,741,273 | A | | 4/1998 | O'Regan | 606/140 |
| 6,126,594 | A | * | 10/2000 | Bayer | 600/184 |
| 6,142,931 | A | * | 11/2000 | Kaji | 600/114 |
| 6,315,713 | B1 | * | 11/2001 | Takada | 600/114 |
| 6,503,192 | B1 | * | 1/2003 | Ouchi | 600/114 |

* cited by examiner

*Primary Examiner*—Gary Jackson
(74) *Attorney, Agent, or Firm*—Graybeal Jackson Haley LLP

(57) ABSTRACT

An anoscope for use with a medical instrument insertable within the interior of the anoscope. The anoscope comprises a tubular member having a longitudinal axis with a proximal end and a distal end. The distal end is insertable into the rectum of a patient while the proximal end remains outside the body. A first longitudinal slot extends from the distal end toward the proximal end, and a second longitudinal slot extends from the proximal end toward the distal end. The first and second longitudinal slots are separated by about 180° on the surface of the tubular member. The first longitudinal slot is adapted to permit access to a site to be treated within the rectum and the second longitudinal slot is adapted to accommodate pivoting of the medical instrument at an angle to the longitudinal axis of the tubular member to improve access to the site to be treated.

14 Claims, 3 Drawing Sheets

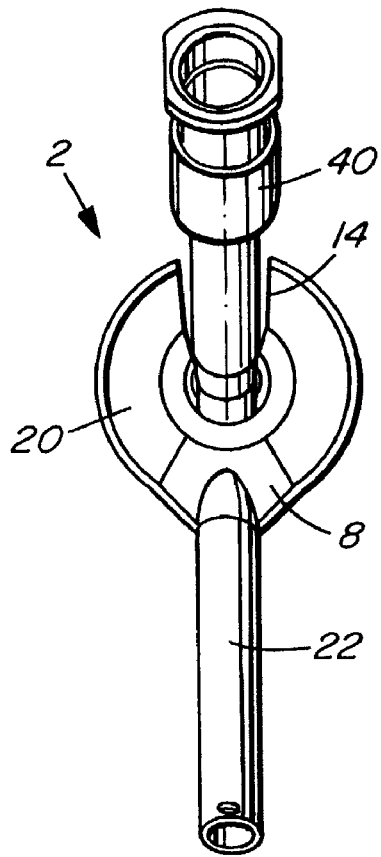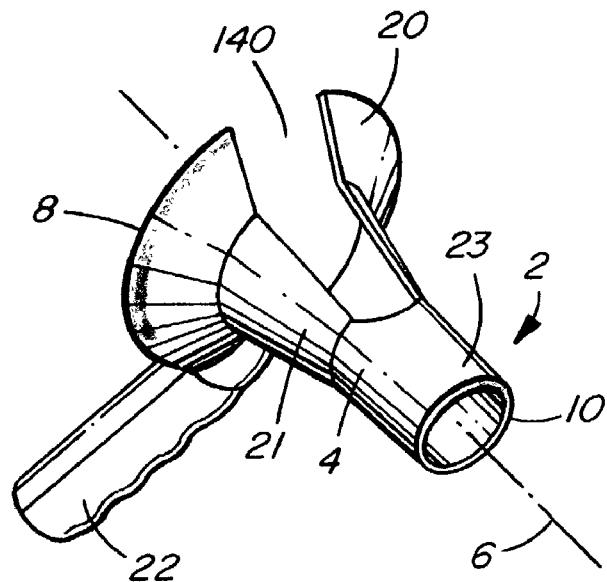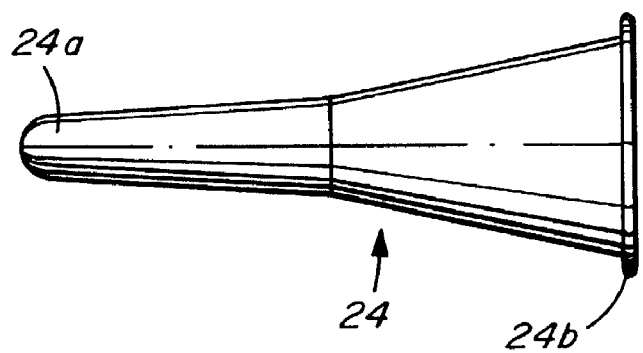
FIG. 6
FIG. 8
FIG. 7

ANOSCOPE

CROSS-REFERENCE TO RELATED APPLICATIONS

The present application claims priority from Canadian patent application 2,363,473, filed Nov. 20, 2001.

BACKGROUND OF THE INVENTION

1. Field of Invention

The present invention relates to a speculum medical device to permit access to treatment sites in the rectum and colon, and, in particular, to an anoscope that is useful in the treatment of hemorrhoids.

2. Background of the Invention

A medical device to permit access to an orifice of the human body is referred to generally as a speculum. Equipment for dilating and inspecting the anus, rectum and colon of a patient is often referred to as an anoscope. An anoscope generally comprises a hollow tubular member that is inserted into the anus and colon. The tubular body dilates the anus and covers the skin of the anal canal. The inner or distal end of the equipment enters the rectum and colon. The distal end is often formed with a gap, notch or slot which is positioned over the site of interest. The interior of the tubular member provides a viewing and access passage for the doctor to inspect and perform procedures at the site of interest. Anoscopes are particularly useful in the inspection and treatment of hemorrhoids. The hemorrhoidal tissue is centred in the notch at the distal end and the tissue tends to bulge into the tubular interior of the anoscope for ready access by a doctor. The tissue may be inspected, sutured or other procedures performed such as a biopsy. An example of a typical anoscope is disclosed in U.S. Pat. No. 4,834,067 to Block.

A common surgery performed in conjunction with an anoscope is a hemorrhoidectomy which involves excision of the hemorrhoid tissue and suturing of the surgically produced wounds. The patient is usually placed under general anesthesia, which entails an inherent degree of risk. In addition, the patient invariably experiences acute pain for many days during the period of recovery, especially when defecating.

The treatment of hemorrhoids by elastic band ligation is credited to Blaisdell who described this technique in Diseases of the Colon and Rectum in 1963. The technique involves placing an elastic band on tissue in the rectum above the area of the hemorrhoid where there is little sensation. The tissue trapped in the band being cut off from its blood supply degenerates and is sloughed, and the elastic band along with the sloughed tissue is passed with the bowel motions. More importantly, however, the resulting healing process causes the tissue in the vicinity to become fixed and prolapse of the hemorrhoidal tissue is minimized. Furthermore, the elastic band ligation technique has been found to give relief of hemorrhoidal symptoms.

Commonly owned U.S. Pat. No. 5,741,273 entitled "Elastic band ligation device for treatment of hemorrhoids" discloses a special tool that is useful for elastic banding of hemorrhoids to avoid suturing. The disclosure of U.S. Pat. No. 5,741,273 is incorporated herein by reference. An advantage of the patented ligation device is that the device may be used without directly seeing the site for banding. Thus, it may be used without an anoscope or any other type of scope or viewing technique. The ligation device is sufficiently small that it can be inserted into the rectum of a patient without major discomfort. For best results, however, the elastic band ligation device is used with an anoscope so that the doctor see the site of interest immediately prior to banding.

In order to provide adequate room for manipulation of the elastic band ligation device or any other inspection or treatment instrument within the interior of an anoscope, it has previously been preferable to use larger diameter anoscopes that are often uncomfortable for the patient. With anoscopes having a diameter larger than 2 to 2½ inches, depending on the patient, it is generally necessary to perform the procedure in an operating room under a general anesthetic which increases the risk and cost of the procedure. The cost of the anesthetic, the operating room and the recovery room can be in the order of $1000 per procedure.

There is therefore a need for an anoscope that is designed to be of sufficiently small diameter that it can be used without requiring a general anesthetic while at the same time permitting manipulation of a medical instrument inserted into the anoscope for improved access to the site of interest in the distal notch of the anoscope.

SUMMARY OF THE INVENTION

The present invention provides an anoscope that is of appropriate diameter for insertion without discomfort into the anus of a patient which includes a proximal notch in addition to the distal notch. The proximal notch remains external to anus and accommodates pivoting of a medical instrument inserted into the interior of the anoscope off the longitudinal axis of the anoscope to improve access to the site of interest in the distal notch.

Accordingly, the present invention provides an anoscope comprising a tubular member of sufficient length for insertion into the rectum of a patient having a longitudinal axis with a proximal end and a distal end at opposite ends of the longitudinal axis, a first longitudinal slot extending from the distal end toward the proximal end a distance along the tubular member, and a second longitudinal slot extending from the proximal end toward the distal end a distance along the tubular member, said first and second longitudinal slots being separated by about 180° on the surface of the tubular member.

The present invention also provides an anoscope comprising a tubular member having a proximal end and a distal end, a first longitudinal slot extending from the distal end to part way along the tubular member, and a second longitudinal slot extending from the proximal end to part way along the tubular member, said first and second longitudinal slots being separated by about 180° on the surface of the tubular member.

The present invention also provides an anoscope for use with a medical instrument insertable within the anoscope, comprising a tubular member having a longitudinal axis and a proximal end and a distal end, a first longitudinal slot extending from the distal end toward the proximal end, and a second longitudinal slot extending from the proximal end toward the distal end, the first and second longitudinal slots being separated by about 180° on the surface of the tubular member, the first longitudinal slot being adapted to permit access to a site to be treated and the second longitudinal slot being adapted to accommodate pivoting of the medical instrument at an angle to the longitudinal axis of the tubular member.

In a further aspect, the present invention provides an anoscope comprising a tubular member of sufficient length for insertion into the rectum of a patient having a longitudinal axis with a proximal end and a distal end at opposite ends of the longitudinal axis, with a longitudinal slot extending from the proximal end toward the distal end a distance along the tubular member adapted to accommodate pivoting of the medical instrument at an angle to the longitudinal axis of the tubular member.

The anoscope of the present invention is preferably disposable and formed from a transparent, medical grade plastic to improve visibility for the doctor. The distal and proximal notches do not intersect and are spaced apart so that rigidity of the tubular member is maintained to prevent collapse of the tubular member against the pressure exerted by rectal muscles of the patient.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Aspects of the present invention In drawings which illustrate embodiments of the invention.

FIG. 2 is a rear perspective view of the anoscope of FIG. 1a;

FIG. 6 is a rear elevation view of the combined anoscope and ligation tool of FIG. 4;

FIG. 7 is an elevation view of an obturator device for use with the anoscope of the present invention to permit insertion into the anus of a patient.

FIG. 8 is a perspective view of an alternative embodiment of the anoscope of the present invention having only a proximal slot.

DETAILED DESCRIPTION OF THE PREFERRED EMBODIMENTS

Figure 1:
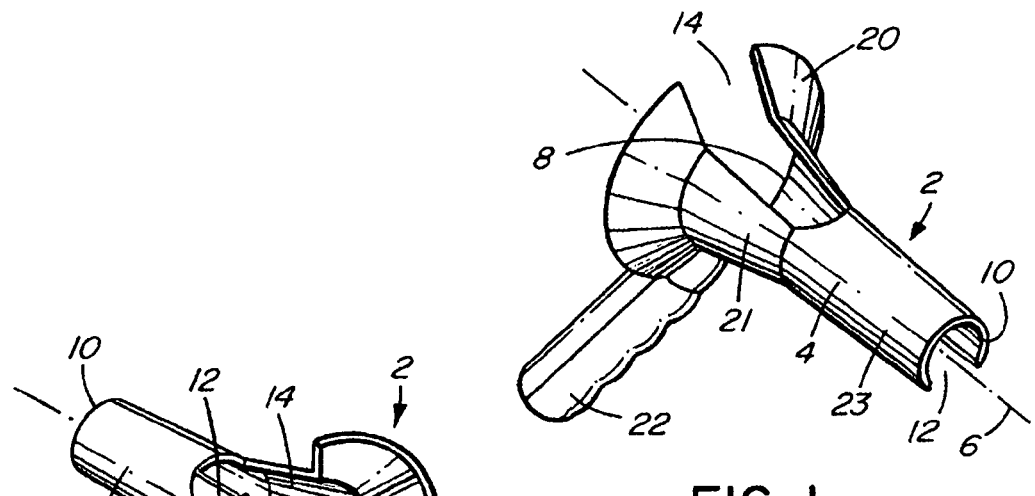
FIG. 1 is a front perspective view of a first embodiment of an anoscope according to the present invention.
Figure 2:
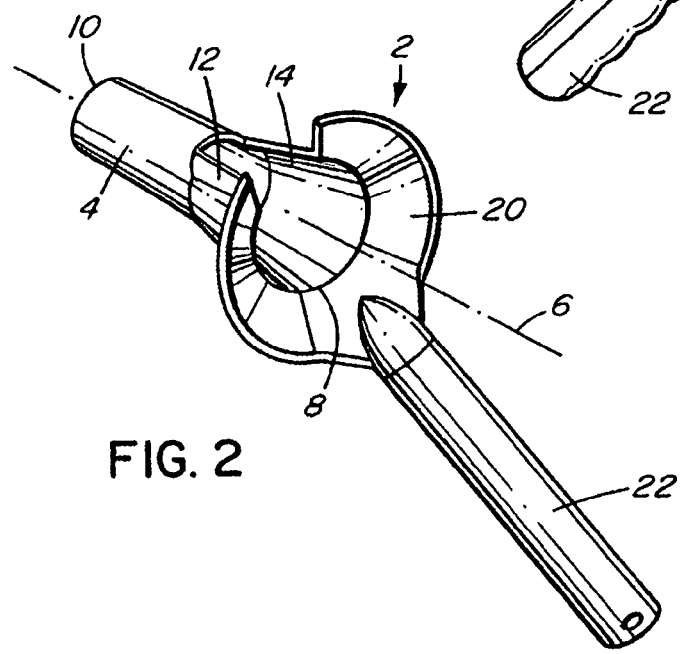
Figure 3:
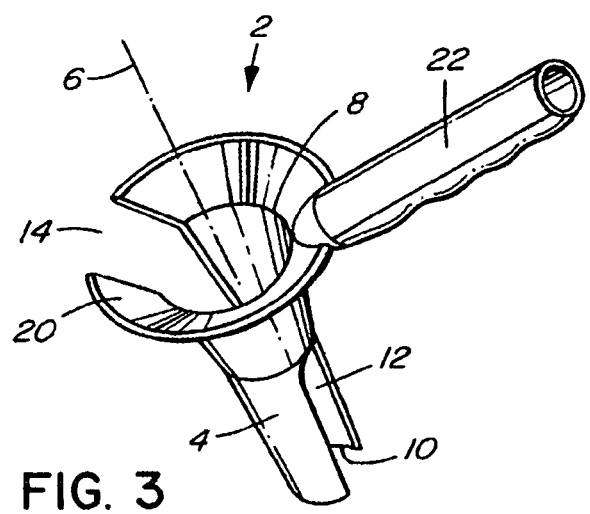
FIG. 3 is an additional rear perspective view from a different angle to clearly show the distal and proximal notches of the anoscope.

Referring to FIGS. 1–3, there are shown various views of a preferred embodiment of an anoscope 2 according to the present invention. Anoscope 2 comprises a tubular member 4 of sufficient length for insertion into the rectum of a patient. Tubular member 4 defines a hollow body having a longitudinal axis 6 with a proximal end 8 and a distal end 10 at opposite ends of the longitudinal axis. A first longitudinal slot 12 extends from distal end 10 toward proximal end 8 a distance along the tubular member. Similarly, a second longitudinal slot 14 extends from proximal end 8 toward the distal end a distance along the tubular member. First and second longitudinal slots 12 and 14 are separated by about 180° on the surface of the tubular member.

Tubular member 4 is formed with an outwardly flaring generally frusto-conical flange 20 adjacent the proximal end 8 which is intersected by slot 14. Tubular member 4 tapers inwardly towards distal end 10 to facilitate insertion of the tubular member into the anus and rectum of a patient. In the illustrated embodiment, the taper occurs over two stages to divide the tubular member into a first generally conical portion 21 near the proximal end and a second conical portion 23 adjacent the distal end. The body of tubular member 4 is preferably formed from a transparent medical grade plastic that can be readily disposed of after use.

An obturator 24 (FIG. 7) is used with the anoscope to provide a single composite structure during insertion. The obturator slides lengthwise within anoscope 2 to extend along axis 6. The obturator has a domed or bullet-nose front portion 24a that protrudes from proximal end 10. The obturator has a body that is generally conical in shape to conform to the shape of the interior of the tubular member in order to fill slots 12 and 14. The obturator is somewhat longer than the tubular member so that flange 24b protrudes from flange 20 to serve as a gripping surface 24b to remove the obturator when the anoscope has been inserted.

Preferably, a handle 22 extends from flange 20 at proximal end 8 for grasping by the doctor on insertion of the anoscope. Handle 22 is preferably located on the same side of the tubular member as the first longitudinal slot 12 to ensure that the tubular body of the anoscope is as strong and rigid as possible.

Figure 5:
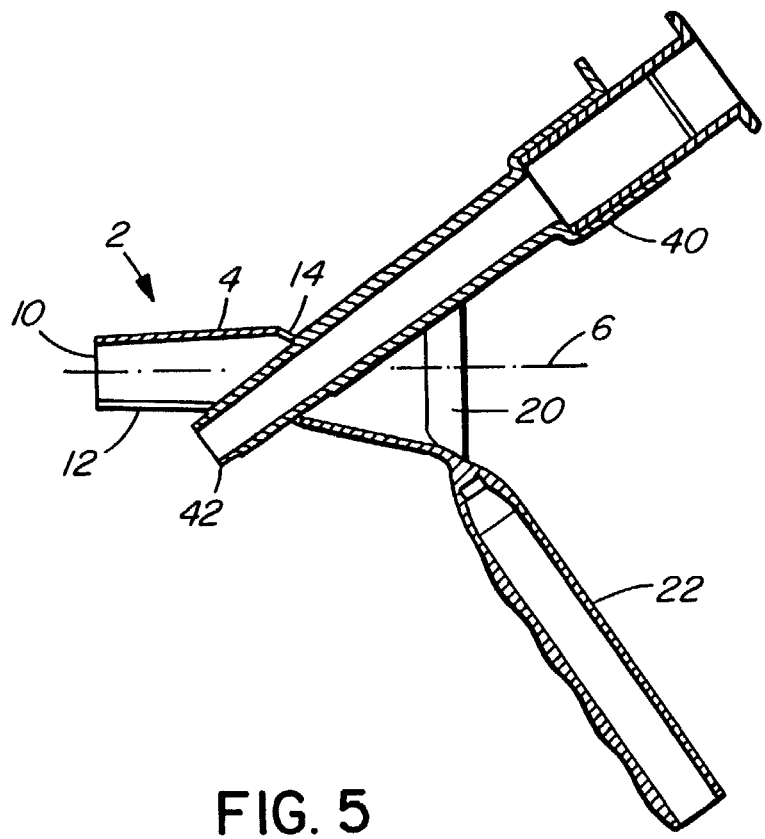
FIG. 5 is a cross-section taken through FIG. 4.

As best shown in FIG. 5, handle 22 is preferably hollow to accommodate the insertion of an illumination device, such as a penlight, into the interior of the handle. The penlight serves to illuminate by internal reflection of light, the transparent plastic walls of the anoscope to allow the doctor an improved lighted view of the tissues dilated by the anoscope. Such illumination means is conventionally a part of examining and operating anoscopes.

Figure 4:
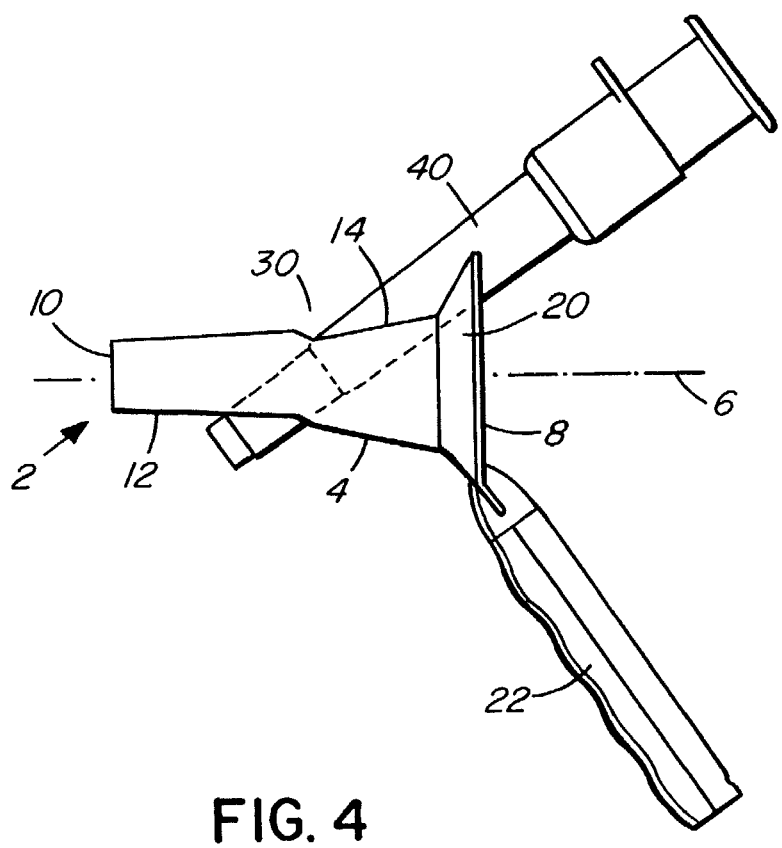
FIG. 4 is a side elevation view of the anoscope with an inserted ligation tool.

Referring to FIG. 4, first longitudinal slot 12 and second longitudinal slot 14 are preferably dimensioned to overlap in a region 30 intermediate the ends of tubular member 4. This arrangement is preferred as it maintains the structural rigidity of the tubular body against the involuntary muscular contractions of the patient and readily permits pivoting of a medical instrument inserted into the interior of the anoscope at an angle to the longitudinal axis 6 of the tubular member.

FIGS. 4, 5 and 6 illustrate a medical instrument 40 inserted into the interior of anoscope 2 and pivoted at an angle to the longitudinal axis 6 of the anoscope. FIG. 5 is a section view taken through FIG. 4 and FIG. 6 is a rear end view of the arrangement shown in FIG. 4. The illustrated medical instrument 40 is the elastic band ligation device described and claimed in commonly owned U.S. Pat. No. 5,741,273. This instrument is particularly suited for use with the anoscope of the present invention as it is important that the tip 42 of the instrument be correctly positioned over a hemorrhoid site in distal slot 12 to allow the hemorrhoid to be drawn by suction into the interior of 42 for the subsequent banding operation. It will be appreciated by those skilled in the art that the anoscope of the present invention will find application with other medical devices that are introduced through the interior of the anoscope and that require being pivoted off the axis 6 of the anoscope through proximal slot 14 for optimal access to the site of interest at distal slot 12

The anoscope of the present invention is of a sufficiently small diameter that it can be inserted without resorting to a general anesthetic. The reduced interior space within the anoscope for manipulating a medical instrument is substantially offset by longitudinally extending slot 14 which co-operates with slot 12 to permit improved maneuverability of the instrument by pivoting of the instrument to an angle with respect to the longitudinal axis 6 of the anoscope. For example, in FIGS. 4 and 5, instrument 40 is shown pivoted at an angle of approximately 35° to axis 6 of the anoscope which significantly improves the ability of a doctor to position working tip 42 of the instrument correctly at the site of interest in slot 12 despite the smaller diameter of the tubular body of the anoscope.

In use, the anoscope 2 is inserted into the anus and the rectum of a patient. During insertion, obturator 24 fills the proximal end 10 of the anoscope and slots 12 and 14. Frusto-conical flange 20 is positioned adjacent and shields the patient's anus. The tubular body of the anoscope dilates the anus and covers the skin of the anal canal. The proximal end 10 enters the rectum. After insertion of the anoscope, the obturator is withdrawn from proximal end 8 to clear slots 12 and 14. The tubular member 4 maintains the anus firmly distended despite a tendency of the sphincter to contract. Particularly when no anaesthetic is used, this tendency of the anus to contract is strong. Transparent tubular member 4 assures a clear view of the hemorrhoid. When slot 12 of proximal end 10 is centered at a hemorrhoid, the tissue bulges into the space provided by the slot so that the tissue is positioned for inspection and/or treatment whether by elastic band ligation, suturing or some other technique. Despite any involuntary muscular constriction, the tubular member maintains the anal canal dilated to maintain an adequate view of the rectum. Moreover, flange 20 and the tubular body act as a shield for the anus and the anal canal against the instrument used in the procedure. This is particularly important for a fully conscious patient when no anaesthetic is used and when some local anaesthetic is used. The tissue of the rectum is virtually insensitive to pain.

In a preferred arrangement that is suitable for use with the majority of patients, the anoscope of the present invention is preferably 3½ inches long with an internal diameter that tapers from 1⅜ inches at proximal end 8 to ¾ inches at distal end 10. Slot 12 extends for approximately 1⅞ inches along the body and slot 14 extends for approximately 2 inches along the body of the tubular member. Flange 20 is about about 2¼ inches in diameter at its widest point.

FIG. 8 is a perspective view of an alternative embodiment of the anoscope of the present invention having only a longitudinally extending proximal slot 140. The presence of a proximal slot alone is sufficient to enjoy the advantage of improved maneuverability of a medical instrument inserted into the interior of the anoscope. Slot 140 permits angling of the instrument off the longitudinal axis 6. To increase the angle to which the inserted medical instrument can be pivoted, distal conical portion 23 is preferably shortened as compared to longer portion 23 in the embodiment of FIG. 1.

While specific embodiments of the invention have been described and illustrated, such embodiments should be considered illustrative of the invention only and not as limiting the invention as construed in accordance with the accompanying claims.

What is claimed is:

1. An anoscope comprising a tubular member of sufficient length for insertion into the rectum of a patient having a longitudinal axis with a proximal end and a distal end at opposite ends of the longitudinal axis, a first longitudinal slot extending from a distal edge toward the proximal end a distance along the tubular member, and a second longitudinal slot extending from a proximal edge toward the distal end a distance along the tubular member, said first and second longitudinal slots being separated by about 180° on the surface of the tubular member.

2. The apparatus of claim 1 wherein the tubular member is tapered inwardly towards the distal end to facilitate insertion of the tubular member into the rectum.

3. The apparatus of claim 2 wherein the tubular member adjacent the proximal end is flared outwardly.

4. The apparatus of claim 3 wherein the tubular member flares into a frusto-conical flange adjacent the proximal end.

5. The apparatus of claim 3 further comprising a handle extending from the proximal end.

6. The apparatus of claim 5 wherein the handle is located on the same side of the tubular member as the first longitudinal slot.

7. The apparatus of claim 5 wherein the apparatus is made of transparent plastic.

8. The apparatus of claim 7 wherein the handle is hollow and able to accommodate the insertion of an illumination device into the handle.

9. The apparatus of claim 1 wherein the first longitudinal slot and the second longitudinal slot are dimensioned to overlap in a region intermediate the ends of the tubular member.

10. The apparatus of claim 1 including an obturator fitting insertable within the tubular member having a rounded front portion protrudable from the distal end and a body portion to fill the longitudinal slots of the tubular member to assist insertion into the rectum.

11. An anoscope comprising a tubular member having a proximal end and a distal end, a first longitudinal slot extending from the distal end to part way along the tubular member, and a second longitudinal slot extending from a proximal edge to part way along the tubular member, said first and second longitudinal slots being separated by about 180° on the surface of the tubular member.

12. The apparatus of claim 11 wherein the first longitudinal slot and the second longitudinal slot are dimensioned to overlap in a region intermediate the ends of the tubular member.

13. An anoscope for use with a medical instrument insertable within the anoscope, comprising a tubular member having a longitudinal axis and a proximal end and a distal end, a first longitudinal slot extending from a distal edge toward the proximal end, and a second longitudinal slot extending from a proximal edge toward the distal end, the first and second longitudinal slots being separated by about 180° on the surface of the tubular member, the first longitudinal slot being adapted to permit access to a site to be treated and the second longitudinal slot being adapted to accommodate pivoting of the medical instrument at an angle to the longitudinal axis of the tubular member.

14. The apparatus of claim 13 wherein the first longitudinal slot and the second longitudinal slot are dimensioned to overlap in a region intermediate the ends of the tubular member.

* * * * *

UNITED STATES PATENT AND TRADEMARK OFFICE
CERTIFICATE OF CORRECTION

| | | |
|---|---|---|
| PATENT NO. | : 7,029,438 B2 | |
| APPLICATION NO. | : 10/301492 | |
| DATED | : April 18, 2006 | |
| INVENTOR(S) | : G. Morin et al. | |

It is certified that error appears in the above-identified patent and that said Letters Patent is hereby corrected as shown below:

Column 1 line 50 change "comprising" to -- wherein the anoscope comprises--
Column 2 line 29 change "comprising" to -- wherein the anoscope comprises--
Column 2 line 31 change "the distal end" to --a distal ege--
Column 2, line 41 change "comprising" to --wherein the anoscope comprises--

Signed and Sealed this

First Day of August, 2006

JON W. DUDAS
*Director of the United States Patent and Trademark Office*